(12) United States Patent
Udo et al.

(10) Patent No.: US 7,298,462 B2
(45) Date of Patent: Nov. 20, 2007

(54) METHOD FOR MOBILE ON AND OFF-LINE MONITORING OF COLORED AND HIGH-GLOSS AUTOMOBILE COMPONENT SURFACES

(75) Inventors: Pecher Udo, Hof (DE); Horst Abendschein, Feuchtwangen (DE)

(73) Assignee: Rehau AG & Co., Rehau (DE)

( * ) Notice: Subject to any disclaimer, the term of this patent is extended or adjusted under 35 U.S.C. 154(b) by 347 days.

(21) Appl. No.: 10/497,468

(22) PCT Filed: Apr. 16, 2002

(86) PCT No.: PCT/EP02/04192

§ 371 (c)(1),
(2), (4) Date: Jun. 2, 2004

(87) PCT Pub. No.: WO03/054529

PCT Pub. Date: Jul. 3, 2003

(65) Prior Publication Data
US 2005/0018173 A1    Jan. 27, 2005

(30) Foreign Application Priority Data
Dec. 21, 2001   (DE) ................................ 101 63 596

(51) Int. Cl.
*G01B 9/02*   (2006.01)
*G01J 3/46*   (2006.01)

(52) U.S. Cl. ........................ 356/73; 356/451; 356/402

(58) Field of Classification Search .................. 356/73, 356/451, 402
See application file for complete search history.

(56) References Cited

U.S. PATENT DOCUMENTS

| 4,989,981 A | 2/1991 | Kawamura et al. |
| 5,387,977 A | 2/1995 | Berg et al. |
| 6,320,654 B1 * | 11/2001 | Alders et al. ............. 356/237.2 |
| 6,768,814 B1 | 7/2004 | Spitzer et al. |
| 2001/0036309 A1 | 11/2001 | Hirayama et al. |

FOREIGN PATENT DOCUMENTS

| DE | 197 39 250 A | 3/1998 |
| DE | 197 09 406 A | 4/1998 |

\* cited by examiner

*Primary Examiner*—Roy M. Punnoose
(74) *Attorney, Agent, or Firm*—Venable LLP; Robert Kinberg; Ryan M. Flandro

(57) ABSTRACT

A method for mobile on- and off-line monitoring of coloured and high-gloss automobile component surfaces includes a camera-supported optical scanning of the automobile surface by means of an angle-dependent spectrophotometer, connected to and initialising an optical neuro-fuzzy structured image data bank, which permits a preparation of the measured signal coming from the detector by means of a computer-aided optical quality data bank and allows an evaluation of the measured automobile surfaces. The data link occurs via a neuronal network to a control unit for surface measurement systems, connected to a production planning system, a customer information system and the product unit for automobile painting/coating.

11 Claims, 1 Drawing Sheet

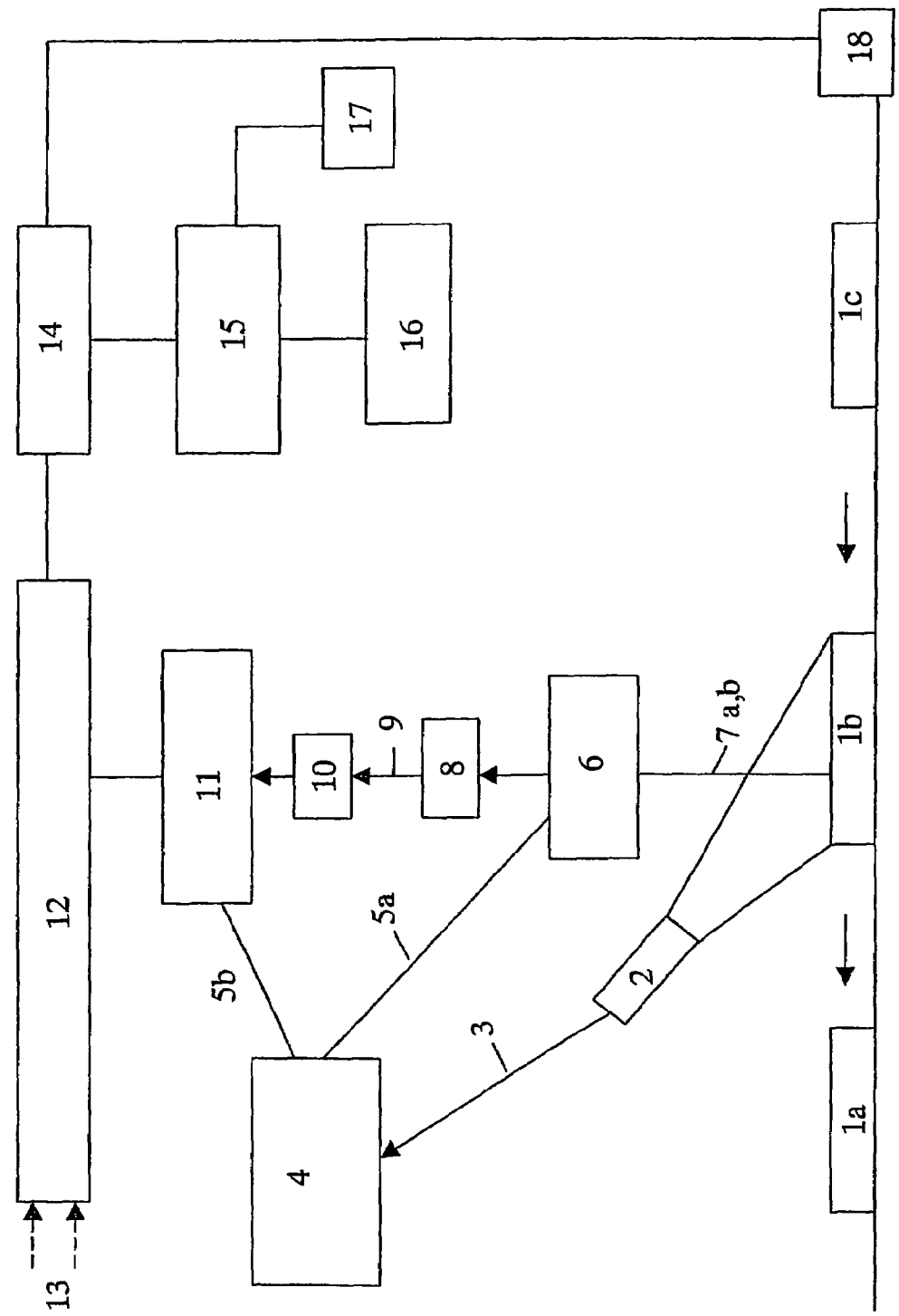

METHOD FOR MOBILE ON AND OFF-LINE MONITORING OF COLORED AND HIGH-GLOSS AUTOMOBILE COMPONENT SURFACES

BACKGROUND

1. Field of the Invention

The invention relates to a method for mobile on-line and off-line monitoring of colored and high-gloss automobile component surfaces. For evaluating the surface quality of series-produced coated and/or painted automobile body components, it is standard procedure at the present time to analyze quality parameters such as color, gloss, layer thickness and wave (waviness) to determine different characteristics, dependencies and parameters. Commercially available manual measuring devices are used for this, for example the angle spectrometer X-Rite MA 68 II and gloss-measuring devices such a Wave Scan plus by the company BYK-Gardner GmbH, 82534 Geretsried.

For measuring the colored and high-gloss automobile component surfaces, coating samples—so-called test panels—are generally produced which are then used to determine the optical characteristics to be examined, such as color, gloss, layer thickness and wave of the coating, as well as to analyze the mutual dependencies of the coating characteristics.

As a rule, this is done in the laboratory or during the production by taking random samples using the aforementioned measuring methods and devices.

2. Related Art

Reference DE 19709406 A1 discloses a method and a device for measuring painted test panels to determine the surface quality—color, gloss, layer thickness and wave—with the aid of a laboratory robot in combination with a corresponding measuring method.

The disadvantage of this method and device is that the evaluation of the measuring results with the aid of test panels does not take into account the geometric form of automobile component surfaces, thus allowing only indirect conclusions to be drawn for the quality analysis.

Reference DE 19717593 A1 discloses a measuring method for evaluating the surface quality of motor-vehicle bodies by detecting in a non-contacting manner the surfaces of series-produced, automatically coated motor vehicle components in conjunction with a multi-axis robot moving along pre-programmed movement paths.

This invention has the disadvantage of high investment costs for the robot required for use and the associated program-technical links for controlling its measuring movement along the automobile component surface to be measured, as well as the stationary connection.

Also known from prior art are non-contacting measuring techniques using cameras, which are aimed at defined angles onto the automobile component surfaces to be measured and which measure these surfaces under various types of lighting and lighting angles.

However, these measuring techniques do not meet the requirements of the automobile industry with respect to mobile use, degree of automation, low investment costs, flexibility of the measuring requirements, ability to simultaneously measure various measuring variables such as color, gloss, layer thickness and wave and the option of a data-technical analysis. Furthermore, a variable measuring of critical automobile component surface parameters on-line and off-line is not possible with the presently used methods, but is desired by the automobile industry.

It is the object of the present invention to develop a method that allows a mobile on-line and off-line monitoring of the quality of colored and high-gloss automobile component surfaces, so that parallel measurements of the parameters for color, gloss, layer thickness and wave can be realized quickly and structured according to different requirements. The core of the invention is the mobile on-line or off-line measuring through optical scanning of the colored and high-gloss automobile component surfaces with an angle-dependent spectrophotometer during the production or final control.

The measuring beam, formed with polarized light of different wave lengths, is thus the measuring beam for the angle-dependent spectrophotometer which is combined with a reference beam for the angle-dependent spectrophotometer and contains the reflection, interference, depolarization and phase values of the measured automobile component surface for different wavelengths as surface information, wherein these represent locally precise images of the optical surface conditions of the automobile component surfaces.

The electronic camera system is embodied as image-recognition system, which detects ahead of time the shape and position of automobile component surfaces to be measured optically with a spectrophotometer. The system carries out a form and position identification with the aid of the electronic databank, embodied as optical neuro-fuzzy structured image databank, and then initiates an optical-angle dependent spectrophotometer measurement, defined for this form and position, for the identified and classified automobile component surface, using predetermined measuring parameters such as wavelength, measuring angle, type of combination measuring—that is to say a measuring and scanning for color, gloss, layer thickness and wave.

The form of the automobile component surface is identified with the aid of electronic classes of automobile component surfaces which are stored object-related in the optical neuro-fuzzy structured image databank.

The neuro-fuzzy techniques are known in principle from the literature and have been used for years in different areas of the industry, that is for modeling, analysis, monitoring and control of industrial processes.

In contrast to the above methods, the method according to our invention distinguishes itself in that it is faster, meets more comprehensive object-specific measuring requirements and allows the classifying of measuring tasks with respect to the automobile component surfaces.

The present invention uses an optical neuro-fuzzy structured image databank in which the automobile component surface images are stored together with the associated measuring techniques. A camera image for comparing the image-patterns on the automobile component surface permits an allocation and/or classification of the measuring object and, following the object detection, controls the object-specific measuring technique of the angle-dependent spectrophotometer for the integral color, gloss, layer thickness and wave measuring with respect to the identified automobile component surface.

Deviations in color, gloss, layer thickness and wave of the measured automobile component surfaces, including different automobile components, are stored object-specific and component-specific in a computer-aided optical quality databank, called a CAOQ databank, for the optical characterization. This CAOQ databank computes and administers as databank logical links, measured integrally for the various automobile component surfaces at different object points to obtain color, gloss, layer thickness and wave data and compares these data to required specified datasets for desired values predetermined by the automobile manufacturer for the automobile component surfaces as target values and tolerances. The data are transmitted with standardized statistic methods, outlier analyses, graphic representations of color, gloss, layer thicknesses and wave differences to a test station for surface measuring technology, via intelligent neuronal net, and can be visually displayed for an operator. Thus, the operator at the test station for surface measuring technology can reach a comprehensible decision that can be implemented with respect to the quality of individual, measured automobile component surfaces.

At least two mobile on-line and off-line monitoring methods of the above-described type are advantageously used at different locations during a production and are linked via intelligent neural net to the control station for surface measuring technology.

In a further step, the data and decisions recorded by the control station for surface measuring technology are transmitted to the production planning system, called PPS, via data transmittal and stored electronically for the specific automobile component. In particular, the production planning system records deviations in color, gloss, layer thickness and wave and the values determined with this method are then transmitted back electronically via the net to the production unit for automobile painting/coating, so that the detected deviations can enter into corresponding changes to the automobile painting/coating processes.

In an additional processing step, the transport system for the following automobile component surface to be measured is clock-pulse actuated.

The data are furthermore transmitted via network to a client-information system which transmits data on-line from the supplier to the automobile manufacturer.

BRIEF DESCRIPTION OF THE DRAWING

FIG. 1 is a schematic representation of a device for mobile on-line and off-line monitoring of colored and high-gloss automobile component surfaces according to an The invention is explained in further detail with the exemplary embodiment shown in the drawing. This embodiment shows a schematic representation of a device for realizing the method for the mobile on-line and off-line monitoring of colored and high-gloss automobile component surfaces. Automobile component surfaces $1a$-$1c$ are produced in an automobile component production unit, not shown in further detail herein, and are then transported with the aid of a transport system 18 to the mobile on-line and off-line monitoring. The automobile component surface $1b$, which is measured for example, is optically recorded with a camera 2. A pixel image signal for the automobile component surface $1b$ and its form is present at the output 3 of the camera 2. This information, which contains a pixel image that shows exact details of the surface image of the automobile component surface $1b$, is transmitted to an optical neuro-fuzzy structured image databank 4 in which automobile component surface classes are electronically stored. In this optical neuro-fuzzy structured image databank 4, the real automobile component surface images are compared to the automobile image classes, stored therein, of the image databank 4. Following the identification of the automobile component surface $1b$, the measuring technique associated with the object-class for the on-line and off-line monitoring of the colored and high-gloss automobile component surface $1b$ is initialized radio-wave supported $5a$ for the optical surface determination of color, gloss, layer thickness and wave and the angle-dependent spectrophotometer 6 is started with object-specific settings for the scanning with the measuring beam $7a$. At the same time, the computer-aided optical quality databank 11 is initialized via radio wave $5b$ for the detector signal 10 data recording. The measuring beam $7a$, formed with polarized light of different wavelengths from the angle-dependent spectrophotometer, then scans the automobile component surface $1b$. The de-polarized measuring beam $7b$, which is reflected by the automobile component surface $1b$, travels to the angle-dependent spectrophotometer 6 with detector unit 8, a charge-coupled diode [CCD] array.

The output 9 of detector unit 8 carries a detector signal 10 for the surface conditions relating to color, gloss, layer thickness and wave. This detector signal, which contains reflection, interference, polarization and phase information and includes the values for color, gloss, layer thickness and wave for the automobile component surface $1b$, is transmitted to a computer-aided optical quality databank 11, called CAOQ, which is initialized radio-wave supported $5b$ at point 4. This CAOQ databank 11 computes, compares and administers the detector signals 10 for different object points on the automobile component surface $1b$ and generates color, gloss, layer thickness and wave data that are compared to required data sets specified by the automobile manufacturer. These data are transmitted to different addressees via an intelligent neuronal network 12, which links at least two mobile on-line and off-line monitoring techniques 13 of the above-described type to different addressees and can be visualized on at least one control station for the surface measuring technology 14. The data recorded by the control station for surface measuring technology 14, are transmitted in the following step via electronic network to the production planning system 15, called PPS, and are then electronically stored for the specific automobile component. The deviations recorded in the production planning system 15 relating to color, gloss, layer thicknesses and wave data are transmitted via a different electronic network to the production unit for automobile painting/coating 16 and/or the client information system 17, so that necessary measures relating to automobile painting/coating can be initiated in unit 16. In a further step, the transport system 18 for the automobile components is controlled by the production planning system 15 and is clocked in time, so that the following automobile component surface $1c$ can be recorded and measured in accordance with the above-described method.

The invention claimed is:

1. A method for the mobile on-line and off-line monitoring of colored and high-gloss automobile component surfaces, said method comprising:

storing electronically automobile component surface classes in a first electronic databank, the first electronic databank being an optical neuro-fuzzy structured image databank;

optically scanning the automobile component surfaces with a camera system to produce a pixel image of the automobile component surface;

storing the pixel image of the optically scanned automobile component surface in the first electronic databank;

electronically comparing the stored pixel image of the automobile component surface to the automobile component surface classes stored electronically in the first electronic databank to identify the automobile component surface;

initiating an angle-dependent spectrophotometer based on the identified automobile component surface;

optically scanning the automobile component surface with a polarized measuring beam of the angle-dependent spectrophotometer, the beam being formed with polarized light of different wavelengths;

combining the reflected depolarized measuring beam at the automobile component surface with a reference beam from the angle-dependent spectrophotometer to generate optical surface signals, wherein the optical surface signals contain reflection, interference, polarization, and phase information for defining the automobile component surface with respect to color, gloss, layer thickness, and wave values;

detecting the optical surface signals generated at the automobile component surface with a charge-coupled diode (CCD) array;

generating a detector output signal that characterizes the automobile component surface based on the detected optical surface signals;

storing electronically predetermined values representing desired color, gloss, layer thickness, and wave values for automobile component surfaces in a second electronic databank, the second electronic databank being a computer-aided optical quality (CAOQ) databank;

transmitting the detector output signal to the second electronic databank;

generating measured output information based on the detector output signal;

comparing electronically the measured output information to the predetermined values; and generating compared output data.

2. The method according to claim 1, wherein the optical scanning of the identified automobile component surface with the polarized measuring beam of the angle-dependent spectrophotometer is carried out according to a program associated with the identified automobile component surface.

3. The method according to claim 1, further comprising the step of processing and storing the measured output information for the automobile component surface in the second electronic databank.

4. The method according to claim 1, wherein the measured output information contains information representing characteristics of the automobile component surface at predetermined measurement positions.

5. The method according to claim 1, further comprising transmitting the compared output data via an intelligent neuronal network to a mobile control station for surface measuring technology.

6. The method according to claim 5, wherein the compared output data is is visually displayed for an operator at the mobile control station.

7. The method according to claim 5, further comprising transmitting the compared output data to a production planning system.

8. The method according to claim 7, further comprising transmitting the compared output data to a client information system.

9. The method according to claim 7, further comprising transmitting the compared output data to a production unit for automobile painting/coating.

10. The method according to claim 7, wherein the production planning system is arranged to control and clock in time a transport system for the automobile component surfaces.

11. The method according to claim 1, wherein, when the automobile component surface is identified, the first electronic databank initiates the angle-dependent spectrophotometer and the second electronic databank via a radiowave.

* * * * *

UNITED STATES PATENT AND TRADEMARK OFFICE
CERTIFICATE OF CORRECTION

PATENT NO. : 7,298,462 B2  Page 1 of 1
APPLICATION NO. : 10/497468
DATED : November 20, 2007
INVENTOR(S) : Pecher Udo et al.

It is certified that error appears in the above-identified patent and that said Letters Patent is hereby corrected as shown below:

IN THE SPECIFICATION:

Before line 1 in column 2, please insert the subheading --SUMMARY--.

At column 3, line 39, please change "automobile component surfaces according to an" to --automobile component surfaces according to an exemplary embodiment of the invention.--.

At column 3, between line 39 and line 40, please insert --DETAILED DESCRIPTION--.

Signed and Sealed this

Sixth Day of May, 2008

JON W. DUDAS
*Director of the United States Patent and Trademark Office*